United States Patent [19]

Ganhy et al.

[11] Patent Number: 5,288,936
[45] Date of Patent: Feb. 22, 1994

[54] PROCESS FOR THE SYNTHESIS OF ALKYLATED AROMATIC HYDROCARBONS

[75] Inventors: Jean-Pierre Ganhy, Brussels; Pierre Jacobs, Gooik; Marleen Baes, Heverlee; Johan Martens, Brussels, all of Belgium

[73] Assignee: Interox (Societe Anonyme), Brussels, Belgium

[21] Appl. No.: 768,988

[22] PCT Filed: May 25, 1990

[86] PCT No.: PCT/BE90/00022
§ 371 Date: Jan. 24, 1992
§ 102(e) Date: Jan. 24, 1992

[87] PCT Pub. No.: WO90/14323
PCT Pub. Date: Nov. 29, 1990

[30] Foreign Application Priority Data

May 26, 1989 [FR] France ................... 89 07053

[51] Int. Cl.$^5$ .................................................. C07C 2/66
[52] U.S. Cl. ................................. 585/452; 585/446; 585/467; 502/344
[58] Field of Search .................. 585/467, 446, 452; 502/344

[56] References Cited

U.S. PATENT DOCUMENTS 2,758,140  8/1956  Ipatieff et al. ................ 260/668
4,962,254  10/1990  Fukao et al. ................. 585/452

FOREIGN PATENT DOCUMENTS 0128001  12/1984  European Pat. Off. .
0328940  8/1989   European Pat. Off. .
1259535  1/1972   United Kingdom .

Primary Examiner—Asok Pal
Assistant Examiner—P. Achutamurthy
Attorney, Agent, or Firm—Willian Brinks Hofer Gilson & Lione

[57] ABSTRACT

Process for the synthesis of aromatic alkylated hydrocarbons with a saturated alkyl chain including at least four carbon atoms, according to which an aromatic hydrocarbon, replaced by an alkyl group with a short saturated chain comprising one to three carbon atoms, is made to react with an olefin in the presence of a catalyst made up of at least one alkaline metal or a alkaline metal hydride impregnated on an alumina support. The process is characterised by the fact that the catalyst is prepared in the reaction medium in the presence of the aromatic hydrocarbon with a short alkyl chain by mixing anhydrous alumina with the alkaline metal hydride or with the alkaline metal, and then the olefin is introduced in order to start the reaction.

32 Claims, No Drawings

PROCESS FOR THE SYNTHESIS OF ALKYLATED AROMATIC HYDROCARBONS

BACKGROUND OF THE INVENTION

1. Field Of The Invention

The present invention relates to a process for the manufacture of alkylated aromatic hydrocarbons. It relates more particularly to the manufacture of alkylated aromatic hydrocarbons with an alkyl chain containing at least four carbon atoms by reacting an aromatic hydrocarbon substituted by a short-chain alkyl group containing 1 to 3 carbon atoms with an olefin in the presence of a catalyst.

2. Description Of Related Art

A process for the synthesis of alkylated aromatic compounds, consisting in condensing an aromatic hydrocarbon substituted by a group containing a saturated carbon atom bonded to at least one hydrogen atom with an unsaturated hydrocarbon (U.S. Pat. No. 2,758,140, V. N. Ipatieff et al;) column 2, lines 19 to 45 and column 23, claim 1) has been known for a long time. The process can be performed in the presence of contact agents, such as alumina.

However, this known process has the disadvantage of giving rise to poor selectivities and to relatively low yields of the alkylated aromatic compounds (columns 5 and 6, Table 1).

In British Patent GB-1,259,535 there is a description of a process for alkylating aromatic hydrocarbons in the presence of a catalyst containing an alkali metal or an alkali metal hydride deposited on alumina. The catalyst is prepared before the alkylation reaction by mixing the metal with alumina under a nitrogen atmosphere, followed by a heat treatment at 300° C. for several hours (page 2, lines 15 to 20 and lines 38 to 44). European Patent Application EP-A1-0,328,940 discloses a similar process for the synthesis of alkylated aromatic hydrocarbons, where the catalyst is also prepared in a preliminary stage consisting in treating an alumina with an alkali metal and an alkali metal hydroxide at a temperature of 200° to 600° C. in the presence of small quantities of moisture and in an inert gaseous atmosphere (claim 1, page 12).

These processes have the disadvantage of requiring an additional stage for preparing the catalyst immediately before it is employed in the alkylation reaction. Apart from the additional costs linked with the equipment and the thermal energy which are needed for the heat treatment, these processes involve difficulties in handling the catalysts, as the latter generally have the disadvantage of being pyrophoric.

SUMMARY OF THE INVENTION

The invention is intended to overcome these disadvantages by providing a process which makes it possible to obtain selectivities close to 100% with alkylated aromatic hydrocarbon yields which exceed 90% without requiring the prior preparation of the catalyst.

The invention relates to a process for the synthesis of alkylated aromatic hydrocarbons with a saturated alkyl chain containing at least four carbon atoms comprising reacting an aromatic hydrocarbon substituted by a saturated short-chain alkyl group containing one to three carbon atoms with an olefin in the presence of a catalyst comprising at least one alkali metal or an alkali metal hydride impregnated onto an alumina support, wherein the catalyst is prepared in the reaction medium in the presence of the aromatic hydrocarbon substituted by the saturated short-chain alkyl group by mixing anhydrous alumina with the alkali metal or with the alkali metal hydride, and the olefin is then introduced to start the reaction.

The invention is directed to the preparation of aromatic hydrocarbons alkylated by a linear or branched saturated alkyl chain containing more than four and, preferably, not at least eight carbon atoms. It is applicable, in particular, to the preparation of benzene-related hydrocarbons alkylated by a saturated and branched alkyl chain containing five carbon atoms. It is very particularly suited to the preparation of amylbenzenes, such as, for example, tert-amylbenzene.

DESCRIPTION OF PREFERRED EMBODIMENTS OF THE INVENTION

An aromatic hydrocarbon alkylated with a short chain alkyl group, employed as the starting material according to the invention, is intended to denote any aromatic hydrocarbon containing one or more aromatic rings of five or six carbon atoms and at least one saturated alkyl side chain containing one to three carbon atoms. Benzene-related hydrocarbons containing a single aromatic nucleus are preferred and more particularly preferred are toluene, dimethyl- and trimethylbenzene, ethylbenzene, ethyltoluenes, n-propylbenzene and cumene.

The olefin employed as an alkylating agent must contain a linear carbon chain containing at least two and not more than five carbon atoms, at least two of which are linked by an unsaturated bond of olefinic type. Monoolefins containing only one unsaturated bond are preferred. By way of example, the following olefins can be employed in the process according to the invention: ethylene, propylene, n-butenes, isobutene, butadiene, n-pentenes and methylbutenes.

The catalyst used in the process according to the invention must contain at least one alkali metal or an alkali metal hydride in addition to the alumina support. Any alkali metal may be suitable. However, sodium or sodium hydride are generally preferred because of their good activity and their ready availability. Sodium may be the only alkali metal present with the alumina support; such a catalyst has given excellent results.

An alternative form of the catalyst in accordance with the process of the invention comprises an alumina support and a mixture of alkali metals or of alkali metal hydrides in substantially equal proportions. Another alternative form of the catalyst of the invention comprises such an amount of a single alkali metal or of a single alkali metal hydride that it never exceeds twice the amount of all the other alkali metals or alkali metal hydrides combined present in the catalyst.

Another particularly advantageous alternative form of the catalyst of the invention comprises a main alkali metal or alkali metal and small quantities, not exceeding a few percent, of one or two other alkali metals or alkali metal hydrides as a promoter, which are added to the alumina support. The mixture of sodium or of sodium hydride with from 0.1 to 5% of rubidium and/or cesium or rubidium and/or cesium hydride is very particularly worthy of interest.

It is also possible to combine an alkali metal with an alkali metal hydride in one single catalyst.

The quantities of alkali metal or of the alkali metal hydride which are used are in most cases such that the catalyst has an alkali metal/alumina or alkali metal hydride/alumina weight ratio of between 0.02 and 0.50 and, preferably, between 0.08 and 0.20.

According to the invention the alumina support may consist of alumina of different pure or mixed crystalline varieties. $\alpha$, $\beta$ and $\gamma$ alumina varieties are suitable. Good results have been obtained with a support consisting of pure $\gamma$ alumina.

The aluminas employed as the catalyst support in the process according to the invention are porous substances. They generally have a mean pore diameter of between 0.1 and 500 nm. Attractive results have been obtained with aluminas whose mean pore diameter was between 2 and 100 nm. The best results have been obtained by using aluminas with a mean pore diameter of 20 and 30 nm.

The specific surface area of these aluminas must also be within the range from 10 to 360 m$^2$/g of alumina to render effective the alkali metal catalyst mixed with these aluminas. In practice, aluminas whose specific surface area is between 50 and 200 m$^2$/g of alumina are preferred.

The aluminas which are suitable as supports for the alkali metals or alkali metal hydrides in the catalysts in accordance with the process of the invention generally have a pore volume of between 25 and 65 ml/100 g of alumina and, preferably, between 45 and 60 ml/100 g of alumina.

The aluminas used must be free from any traces of free water. If need be, it may be useful to subject them, before they are used as a support for the alkali metal, to a calcination at a temperature of between 200° and 600° C. in order to remove all traces of residual moisture.

The optimum quantities of catalyst are not critical. To ensure good catalyst efficiency, however, it is appropriate that the weight ratio of the alkali metal to the short-chain aromatic hydrocarbon should lie in the range from 0.0015 to 0.03.

An advantageous alternative form of the process according to the invention consists in adding potassium (K) hydroxide during the preparation of the catalyst in the reaction medium. The quantities of the potassium hydroxide which are added are generally such that the weight ratio K hydroxide/alkali metal or alkali metal hydride is between 0.5 and 2 and, preferably, between 0.8 and 1.5.

The temperature and the pressure at which the alkylation reaction in accordance with the process of the invention is performed must be adapted to the nature of the olefin and of the starting aromatic hydrocarbon. It has been found, however, that pressures in the range from 0.5 to 10 MPa and temperatures of between 110° and 250° C. are suitable. Pressures from 1 to 5 MPa and temperatures from 170° to 190° C. have given the best results. When the reaction is performed in the vapour phase it is advantageous to maintain the respective pressures of the olefin and of the starting aromatic hydrocarbon so that the olefin/starting aromatic hydrocarbon molar ratios are within the range from 0.7 to 1.3 and, preferably, about 1.

In order to ensure good contact between the reactants it is generally necessary to perform the reaction with vigorous stirring, in particular when the starting hydrocarbon is liquid and the olefin is gaseous under the reaction conditions. All known types of stirrers are generally suitable. The choice of a particular stirrer is a function of the type of equipment employed for the reactor.

The reaction in accordance with the process according to the invention may be performed in a continuous or noncontinuous reactor, the difference being of no consequence. When the reaction uses a system with two different phases, the continuous reactors may be chosen from conventional reactors, such as stationary-bed or fluidized-bed reactors or moving-bed reactors permitting the circulation and optional regeneration of the catalyst. If three phases are present simultaneously in the reaction system, it is possible to use conventional continuous reactors with a stationary bed (trickle bed) or with a slurry bed. In the case of a noncontinuous reactor, an autoclave fitted with a bladed stirrer is generally used.

The process according to the invention is particularly well-suited for the synthesis of tert-amylbenzene by alkylation of cumene with ethylene.

The examples which follow are intended to illustrate the invention without limiting its scope.

Examples 1R TO 3R (Prior Art)

Into an autoclave of 400-ml capacity, fitted with a bladed stirrer, are introduced 86 g of cumene, 0.43 g of metallic sodium in dispersion in paraffin and 5 g of a support previously dried by heating to 200° C. and chosen from silica, zeolite Y and carbon black.

The autoclave was then closed and heated to 100° C. for 15 minutes with stirring and nitrogen purging. The reaction mixture was then heated to 185° C. and the reaction was started up by injecting ethylene at a pressure of 4.1 MPa into the reactor.

The reaction was allowed to continue for 2.5 hours, after which the amount of tert-amylbenzene (TAB) formed of the residual cumene were determined. The results are given in the following Table 1.

TABLE 1

| Example No. | 1R | 2R | 3R |
|---|---|---|---|
| Nature of the catalyst support | Silica | Zeolite Y | C black |
| Cumene conversion, % | <1 | <1 | <1 |
| Selectivity based on cumene, % | 99 | 99 | 99 |
| TAB yield based on cumene, % | <1 | <1 | <1 |

In this table the conversion based on cumene is equal to 100 times the molar ratio of the cumene consumed to the cumene used, the selectivity based on cumene is equal to 100 times the molar ratio of tert-amylbenzene (TAB) formed to the cumene consumed and the yield based on cumene is equal to 100 times the molar ratio of the tert-amylbenzene formed to the cumene used, that is to say to the product of the above two molar ratios.

It can be seen that the processes of the prior art are ineffective when applied to the synthesis of tert-amylbenzene.

EXAMPLE 4

An Embodiment of The Invention

Example 1 was reproduced by replacing the silica support with a $\gamma$ alumina, designated by Spheralite trademark of SCS79 type, manufactured by Rhône- Poulenc, which exhibited the following characteristics:

| | |
|---|---|
| specific surface area, m²/g | 80 |
| total pore volume, ml/g | 0.6 |
| mean pore diameter, nm | 30 |
| The results obtained were as follows: | |
| cumene conversion, % | 30.8 |
| selectivity based on cumene, % | 99 |
| TAB yield based on cumene, % | 30.5 |

The results clearly show the superiority of the process according to the invention.

EXAMPLES 5 to 9

(Embodiments of The Invention)

Example 4 was reproduced using various grades of alumina and with a modification of the following operating conditions:

| | |
|---|---|
| quantity of sodium: | 0.86 g |
| quantity of support: | 10 g |

The γ aluminas employed were aluminas designated by Spheralite trademark, manufactured by Rhone-Poulenc, which exhibited the characteristics given in detail in Table 2, below:

TABLE 2

| Alumina type | SCS 9 | SCS 79 | SCS 100 | SAS 350 | SAP 350 |
|---|---|---|---|---|---|
| Specific surface area, m²/g | 8 | 80 | 100 | 350 | 350 |
| Total pore volume, ml/100 g | 45 | 60 | 50 | 45 | 23 |
| Mean pore diameter, nm | 300 | 30 | 20 | 5 | 2.5 |

The results obtained are summarized in table 3:

TABLE 3

| Example No. | 5 | 6 | 7 | 8 | 9 |
|---|---|---|---|---|---|
| Alumina type | SCS 9 | SCS 79 | SCS 100 | SAS 350 | SAP 350 |
| Cumene conversion, % | 4.7 | 97.0 | 99.3 | 31.7 | <1 |
| Selectivity based on cumene, % | 99 | 99 | 99 | 99 | 99 |
| TAB yield based on cumene, % | 4.7 | 96.0 | 98.3 | 31.4 | <1 |

The very good results obtained with aluminas SCS 79 and SCS 100 will be noted.

EXAMPLES 10R to 13R (Embodiments Not In Accordance With The Invention)

Example 4 was reproduced, the catalyst being modified as follows:
  Example 10R: only 5 g of alumina of SCS 79 type was used, the sodium being omitted;
  Examples 11R to 13R: only sodium or sodium hydride was used without the alumina support;
  Example 11R: 0.43 g of Na in dispersion in paraffin;
  Example 12R: 0.86 g of Na in dispersion in paraffin;
  Example 13R: 0.86 g of NaH in dispersion in a mineral oil.

The results obtained are given in the following Table 4:

TABLE 4

| Example No. | 10R | 11R | 12R | 13R |
|---|---|---|---|---|
| Nature of the catalyst | SCS 79 alone | Na alone | Na alone | NaH alone |
| Cumene conversion, % | <1 | <1 | 1.5 | <1 |
| Selectivity based on cumene, % | 99 | 99 | 99 | 99 |
| TAB yield based on cumene, % | <1 | <1 | 1.48 | <1 |

The Table 4 results show that catalysts not made in accordance with the invention, consisting solely of the alumina supports of the alkali metal or of a hydride of alkali metal are completely ineffective.

EXAMPLES 14 TO 17

(Embodiments Of The Invention)

Example 4 was repeated, the quantity of sodium being varied with the same single quantity of alumina (10 g). The results are given in Table 5, below.

TABLE 5

| Example No. | 14 | 15 | 16 | 17 |
|---|---|---|---|---|
| Quantity of Na, g | 0.26 | 0.34 | 0.43 | 0.86 |
| Cumene conversion, % | 12.4 | 52.3 | 70.7 | 97.0 |
| Selectivity based on cumene, % | 99 | 99 | 99 | 99 |
| TAB yield based on cumene, % | 12.3 | 51.8 | 70.0 | 96.0 |

EXAMPLES 18 TO 21

Example 6 was repeated, the sodium dispersed in paraffin being replaced with a variable quantity of a dispersion of sodium hydride in a mineral oil.

The results are given in Table 6 below.

TABLE 6

| Example No. | 18 | 19 | 20 | 21 |
|---|---|---|---|---|
| Quantity of NaH, g | 0.1 | 0.2 | 0.27 | 1.13 |
| Cumene conversion, % | <1 | 93.6 | 99.4 | 99.8 |
| Selectivity based on cumene, % | 99 | 99 | 99 | 99 |
| TAB yield based on cumene, % | <1 | 92.7 | 98.4 | 98.8 |

It can be seen that a quantity of sodium hydride as small as 0.2 g is already sufficient to obtain TAB yields of more than 90%.

EXAMPLES 22 TO 25

(Embodiments Of The Invention)

Example 6 was repeated, the reaction temperature being varied.

The results are given in Table 1, below:

TABLE 7

| Example No. | 22 | 23 | 24 | 25 |
|---|---|---|---|---|
| Test temperature, °C. | 169 | 177 | 181 | 185 |
| Cumene conversion, % | <1 | 27.6 | 92.5 | 98.0 |
| Selectivity based on cumene, % | 99 | 99 | 99 | 99 |
| TAB yield based | <1 | 27.3 | 91.6 | 97.0 |

TABLE 7-continued

| Example No. | 22 | 23 | 24 | 25 |
|---|---|---|---|---|
| on cumene, % | | | | |

The results obtained show that the optimum temperature is close to 185° C.

EXAMPLE 26

(Embodiments of The Invention)

Example 6 was reproduced, ethylene being replaced with propylene at a pressure of 0.8 MPa.

After the reaction was conducted for 4 hours with stirring at 185° C., the presence of 2-methyl-2-phenyl-pentane (MPP) and 2,3-dimethyl-2-phenylbutane (DPB) was detected in the reaction mixture. The determination of these products gave the following results:

| | |
|---|---|
| cumene converstion, % | 15.2 |
| selectivity for MPP based on cumene, | 79 |
| selectivity for DPB based on cumene, | 21 |
| yield of MPP based on cumene, | 12.0 |
| yield of DPB based on cumene, | 3.2 |

EXAMPLES 27 TO 30

(Embodiments of The Invention)

Into a stainless-steel autoclave 400 ml in capacity, fitted with a turbine stirring system rotating at 1000 revolutions/min, were introduced 86 g of cumene, 10 g of alumina of trademark EXP 2001 P from Rhône-Poulenc, predried by heating to 200° C., 1 g of alkali metal or alkali metal hydride and optionally 1 g of KOH. Alumina EXP 2001 P has the same characteristics as alumina SCS 79 of Example 6.

The autoclave was then closed and heated to 185° C. for 15 minutes with stirring and a nitrogen purge. Ethylene was then injected into the autoclave at a pressure of 4 MPa. As soon as the reaction commenced, the temperature, pressure and stirring were maintained for 60 minutes.

The results are given in Table 7, below:

TABLE 7

| Example No. | 27 | 28 | 29 | 30 |
|---|---|---|---|---|
| Catalyst type | NaH | NaH | Na | K |
| KOH content, % | 0 | 1 | 1 | 1 |
| Cumene conversion, % | 95.2 | 99.0 | 94.2 | 99.4 |
| Induction period, min | 30 | 0 | 12 | 0 |

The induction period corresponds to the time interval which elapsed between the instant of ethylene injection and the beginning of reaction. In the case of Examples 28 and 30 the reaction was much faster and was stopped after 15 minutes instead of 60 minutes.

The selectivity of the reaction, based on cumene, was approximately 99% in each of the Examples 27 to 30.

EXAMPLES 31 AND 32

(Embodiments of The Invention)

The procedure was as in Examples 27 to 30, except that the quantity of alumina was reduced to 2 g and that of sodium hydride to 0.2 g. Both Examples were carried out in the presence of 0.2 g of KOH during the catalyst preparation. Example 31 was carried out with alumina of trademark EXP 2001 P, Example 32 with alumina EXP 531 P, both manufactured by Rhône-Poulenc and with similar physical characteristics.

The results obtained were as follows:

| Example No. | Reaction time, min | Induction period, min | Cumene conversion, % |
|---|---|---|---|
| 31 | 60 | 3 | 98.4 |
| 32 | 60 | 0 | 97.1 |

The selectivity of the reaction, based on cumene, was approximately 99% in both cases.

EXAMPLES 33R AND 34R

Example 31 was repeated, but the alumina was first treated in a rotary furnace for 2 hours at 500° C. under nitrogen atmosphere. After cooling to 350° C. the alumina was treated with KOH in a proportion of 10% of its weight (Example 33R) and of 5% of its weight (Example 34R) in the same rotary furnace for a period of 3 hours and was then left to cool to room temperature. The procedure followed was then as in Example 31, 2 g of treated alumina and 2 g of sodium hydride being used in the reaction mixture, without addition of KOH to the mixture.

The results obtained were as follows:

| Example No. | Reaction time, min | Induction period, min | Cumene conversion, % |
|---|---|---|---|
| 33R | 60 | >180 | 0 |
| 34R | 60 | 90 | 41.3 |

EXAMPLES 35R AND 36R

Example 31 was repeated but KOH was replaced by NaOH during the catalyst preparation, in a proportion of 0.2 g (Example 35R) and of 0.1 g (Example 36R).

The results obtained were as follows:

| Example No. | Reaction time, min | Induction period, min | Cumene conversion, % |
|---|---|---|---|
| 35R | 60 | 150 | 28.8 |
| 36R | 60 | 114 | 20.5 |

EXAMPLES 37R AND 38R

Examples 33R and 34R were reproduced, except that the treatment of alumina with KOH was followed with an additional treatment of the alumina with metallic potassium in a proportion of 10% of the weight of the initial alumina. The treatment with potassium was continued for 30 minutes at 290° C. and the catalyst thus prepared was then cooled to room temperature. 2 g of catalyst were used in example 37R; in test 38R the catalyst quantity was reduced to 0.4 g.

The results obtained were as follows:

| Example No. | Reaction time, min | Induction period, min | Cumene conversion, % |
|---|---|---|---|
| 37R | 60 | 0 | 94.5 |
| 38R | 60 | >180 | 0 |

We claim:

1. A process for the synthesis of an alkylated aromatic hydrocarbon with a saturated alkyl chain containing at least four carbon atoms, comprising reacting an aromatic hydrocarbon substituted by a saturated short-chain alkyl group containing one to three carbon atoms with a suitable olefin in the presence of a catalyst comprising at least one alkali metal, an alkali metal hydride or a mixture of the alkali metal and the alkali metal hydride impregnated onto an alumina support, the process further comprising preparing the catalyst by mixing the alumina support with the alkali metal, the alkali metal hydride, or the mixture of the alkali metal and the alkali metal hydride in a reaction medium comprising the aromatic hydrocarbon substituted by saturated short-chain alkyl group containing one to three carbon atoms and introducing the olefin, under reaction conditions, into the reaction medium to start the reaction.

2. A process according to claim 1, wherein potassium hydroxide is added to the reaction medium during the catalyst preparation.

3. A process according to claims 1 or 2, wherein the alumina support has a mean pore diameter of between 2 and 100 nm.

4. A process according to claim 3, wherein the alumina support consists of $\gamma$ alumina.

5. A process according to claim 2, wherein the alumina support has a pore volume of between 25 and 65 ml/100 g of alumina and a specific surface area of between 10 and 360 $m^2$/g of alumina.

6. A process according to claim 2, wherein the weight ratio of the alkali metal, the alkali metal hydride, or the mixture of the alkali metal and the alkali metal hydride to the alumina support is between 0.02 and 0.50.

7. A process according to claim 2, wherein the weight ratio of the alkali metal, the alkali metal hydride or the mixture of the alkali metal and alkali metal hydride to the aromatic hydrocarbon substituted by a short-chain alkyl group containing one to three carbon atoms is from 0.0015 to 0.03.

8. A process according to claim 2, wherein the alkali metal is sodium and the alkali metal hydride is sodium hydride.

9. A process according to claim 2, wherein the reaction of the aromatic hydrocarbon substituted by a saturated short chain alkyl group containing one to three carbon atoms with the olefin is performed at a temperature between 170° and 190° C.

10. A process according to claim 1 wherein the saturated alkylated aromatic hydrocarbon containing at least four carbon atoms is tert-amylbenzene, the aromatic hydrocarbon substituted by a saturated short-chain alkyl group containing one to three carbon atoms is cumene and the olefin is ethylene.

11. A process according to claim 2, wherein the alumina support has pore volume of between 45 and 60 ml/g of alumina.

12. A process according to claim 2, wherein the weight ratio of the alkali metal, the alkali metal hydride or the mixture of the alkali metal and alkali metal hydride to the alumina support is between 0.08 and 0.20.

13. A process according to claim 2, wherein the alumina support is free of water.

14. A process according to claim 2, wherein the amount of the potassium hydroxide added is such that the weight ratio of the potassium hydroxide to the alkali metal, the alkali metal hydride or the mixture of the alkali metal and the alkali metal hydride is between 0.5 and 2.

15. A process according to claim 2, wherein the amount of the potassium hydroxide added is such that the weight ratio of the potassium hydroxide to the alkali metal, the alkali metal hydride or the mixture of the alkali metal and the alkali metal hydride is between 0.8 and 1.5.

16. A process according to claim 1, wherein the catalyst comprises a mixture of the alkali metal and the alkali metal hydride.

17. A process according to claim 1, wherein the temperature of the reaction is between 110° and 250° C. and pressure of the reaction is from 0.5 to 10 MPa.

18. A process of claim 1, wherein the catalyst comprises small quantities of a promoter which is one or two alkali metals or alkali metal hydrides different from the alkali metal or the alkali metal hydride of the catalyst.

19. A process of claim 1, wherein the catalyst further comprises a promoter which is a mixture of sodium or of sodium hydride and 0.1 to 5% of rubidium, cesium, a mixture of rubidium and cesium, rubidium hydride, cesium hydride or a mixture of rubidium hydride and cesium hydride.

20. A process for synthesizing an alkylated aromatic hydrocarbon having a saturated alkyl chain containing at least four carbon atoms from an aromatic hydrocarbon substituted by a saturated short-chain alkyl group containing one to three carbon atoms and an olefin, comprising:
   (i) preparing a catalyst in a method comprising adding an alumina support and an alkali metal, an alkali metal hydride or a mixture of the alkali metal and the alkali metal hydride to a reaction medium comprised of the aromatic hydrocarbon substituted by the saturated short-chain alkyl group containing one to three carbon atoms; and
   (ii) initiating the process, under reaction conditions, by introducing into the reaction medium the olefin.

21. A method for preparing a catalyst comprising adding, under reaction conditions, an alumina support and an alkali metal, an alkali metal hydride or a mixture of the alkali metal and the alkali metal hydride to an aromatic hydrocarbon substituted by a saturated short-chain alkyl group containing one to three carbon atoms.

22. The method of preparing a catalyst according to claim 21, wherein said alkali metal, alkali metal hydride or a mixture thereof is sodium, sodium hydride or a mixture thereof.

23. The method of preparing a catalyst according to claim 21, wherein said mixture is a mixture of alkali metals or of alkali metal hydrides in substantially equal proportions.

24. The method of preparing a catalyst according to claim 21, wherein said mixture comprises such an amount of a single alkali metal or of a single alkali metal hydride that it never exceeds twice the amount of all the other alkali metals or alkali metal hydrides combined present in the mixture.

25. The method of preparing a catalyst according to claim 21, which further comprises adding to the aromatic hydrocarbon a promoter which is a mixture of sodium or of sodium hydride and 0.1 to 5% of rubidium, cesium, a mixture of rubidium and cesium, rubidium hydride, cesium hydride or a mixture of rubidium hydride and cesium hydride.

26. The method of preparing a catalyst according to claim 21, wherein the ratio of alkali metal or alkali metal hydride to alumina is between 0.02 and 0.50.

27. The method of preparing a catalyst according to claim 21, wherein said alumina comprises α, β or γ alumina.

28. The method of preparing a catalyst according to claim 21, wherein said alumina has a mean pore diameter of between 0.1 and 500 nm.

29. The method of preparing a catalyst according to claim 21, wherein said alumina has a surface area of between 10 and 360 m$^2$/g of alumina.

30. The method of preparing a catalyst according to claim 21, wherein said alumina has a pore volume of between 25 and 65 ml/100 g of alumina.

31. The method of preparing a catalyst according to claim 21, wherein said alumina is free from any traces of free water.

32. A catalyst produced according to the method of claim 21.

UNITED STATES PATENT AND TRADEMARK OFFICE
CERTIFICATE OF CORRECTION

Page 1 of 2

PATENT NO. : 5,288,936

DATED : February 22, 1994

INVENTOR(S) : Jean-Pierre Ganhy, et al.

It is certified that error appears in the above-indentified patent and that said Letters Patent is hereby corrected as shown below:

Col. 1, line 21, remove the parenthesis after "et al;"

Col. 2, line 8, change "more than" to "at least"

Col. 2, line 9, change "at least" to "more than"

Col. 2, line 58, after "metal" insert "hydride"

Col. 2, line 67, after "of" insert "the"

Col. 4, line 36, after "formed" insert "and"

Col. 4, line 63, insert parenthesis before and after "an Embodiment of the Invention"

Col. 4, line 67, after "trademark" insert a comma

Col. 6, line 16, after "supports" insert a comma

Col. 6, line 59, after "Table" delete "1" and insert "7"

Col. 7, line 44, change "7" to "7a"

UNITED STATES PATENT AND TRADEMARK OFFICE
CERTIFICATE OF CORRECTION

PATENT NO. : 5,288,936
DATED : February 22, 1994
INVENTOR(S) : Jean-Pierre Ganhy, et. al.

It is certified that error appears in the above-indentified patent and that said Letters Patent is hereby corrected as shown below:

Col. 7, line 45, change "7" to "7a"

Signed and Sealed this

Twenty-sixth Day of September, 1995

Attest:

BRUCE LEHMAN

*Attesting Officer*     *Commissioner of Patents and Trademarks*